United States Patent [19]
Allen

[11] Patent Number: 5,128,451
[45] Date of Patent: Jul. 7, 1992

[54] PROTEIN V:A IGG BINDING FACTOR

[76] Inventor: John W. Allen, 2607 Overland Passage, Chapel Hill, N.C. 27516

[21] Appl. No.: 733,219

[22] Filed: Jul. 22, 1991

[51] Int. Cl.$^5$ .................. C07K 3/00; C12N 11/02; C12P 21/02; C07H 15/12
[52] U.S. Cl. .................. 530/350; 435/701; 435/177; 530/387.1; 530/861; 536/27
[58] Field of Search ............... 435/70.1, 177; 530/350, 530/385, 386, 387, 388; 536/27

[56] References Cited

U.S. PATENT DOCUMENTS

| | | | |
|---|---|---|---|
| 4,727,019 | 2/1988 | Valkins et al. | 435/5 |
| 4,757,134 | 7/1988 | Blake et al. | 530/350 |
| 4,883,754 | 11/1989 | Boyle et al. | 435/177 |
| 4,945,157 | 7/1990 | Boyle et al. | 530/409 |
| 4,977,082 | 12/1990 | Boyle et al. | 435/71.1 |
| 5,047,523 | 9/1991 | Woods et al. | 536/27 |

OTHER PUBLICATIONS

Bailey & Scott's *Diagnostic Microbiology* (E. Baron and S. Finegold, Eds.), (8th ed., C.V. Mosby Co., St. Louis, MO) (1990), pp. 575–587, 112.

P. Piot et al., *Journal of Clinical Microbiology 15*, No. 1, 19–24 (1982).

P. Piot et al., *Journal of General Microbiology 119*, 373–396 (1980).

D. Yong and J. Thompson, *Journal of Clinical Microbiology 16*, No. 1, 30–33 (1982).

*Primary Examiner*—David L. Lacey
*Assistant Examiner*—Gian P. Wang
*Attorney, Agent, or Firm*—Bell, Seltzer, Park & Gibson

[57] ABSTRACT

A novel bacterial proteinaceous immunoglobulin G receptor is disclosed. The proteinaceous factor binds all four subclasses of human IgG, as well as rabbit, swine, equine, bovine, sheep, and goat IgG. The proteinaceous factor is obtained from biologically pure cultures of *Gardnerella vaginalis* such as those having the identifying characteristics of ATCC Deposit No. 55195.

7 Claims, 3 Drawing Sheets

PROTEIN V:A IGG BINDING FACTOR

FIELD OF THE INVENTION

The present invention provides materials and methods for extracting and purifying human immunoglobulins. More specifically, the present invention provides a novel bacterial proteinaceous factor that demonstrates affinity for all four subclasses of human IgG.

BACKGROUND OF THE INVENTION

Bacterial Fc receptors have been identified by their ability to bind to a site within the constant region of various classes and subclasses of mammalian IgG. The Fc region of the IgG antibody molecule is associated with the biological effector properties of the molecule, while the antigenic recognition elements are located in the two identical Fab portions of the antibody. Consequently, the interaction of bacterial Fc receptors with constant region determinants on the heavy chain of IgG does not interfere with the ability of the antibody to recognize its antigen. This property makes these receptors useful as tracers of antibody-antigen interaction.

It is known that streptococci and staphylococci bacteria produce proteinaceous factors that bind the Fc region of specific human and animal immunoglobulins. Such proteinaceous factors are also widely used within the industry for extracting and purifying monoclonal antibodies for subsequent application in diagnostics and immunotherapy.

Protein A, the immunoglobulin G(IgG)-binding protein of *Staphylococcus aureus*, was identified in 1966. See A. Forsgren and J. Sjoguist, *J. Immunol.* 97: 822-827 (1966). Immunoglobulin-binding strains of other bacterial species have been described, and especially protein G of group C and G streptococci have been characterized. M. Yarnall et al., *J. Gen. Microbiol.* 32: 2049-2052 (1986); L. Bjorck and G. Kronvall. *J. Immunol.* 133: 969-974 (1984); M. Boyle and K. Reis, Bio/Technology 5: 697-703 (1987).

Boyle and Yarnall (U.S. Patent No. 4,883,754) describe a streptococcus derived proteinaceous factor that specifically binds the Fc region of $IgG_3$ and has a molecular weight of 38 kD. There is also described a separate proteinaceous antigenic factor derived from streptococcus that binds the Fc region of human $IgG_1$, $IgG_2$, and $IgG_4$ having a molecular weight of about 56 kD.

Boyle and Faulmann (U.S. Pat. No. 4,945,157) describe a process for extracting an IgG binding proteinaceous factor, Protein G, from streptococcus. Protein G binds the Fc region of human IgG and reportedly has a molecular weight of about 52 kD.

Boyle and Reis (U.S. Pat. No. 4,977,082) describe a Type VI bacterial receptor for the Fc region of human IgG. The Type VI bacterial receptor has a molecular weight of about 43 kD, and is further characterized in that it binds goat, pig, rabbit, mouse, rat, sheep, cow, and human IgG. Boyle and Reis disclose yet another Type VI bacterial receptor having a molecular weight of about 90 kD and that is present in the culture with the 43 kD protein. The two proteins are separable from other proteins in the concentrated culture supernatant by affinity purification on immobilized goat IgG columns. Both proteins are derived from strains of streptococcus zooepidemicus.

SUMMARY OF THE INVENTION

The present invention provides a novel bacterial immunoglobulin binding protein, protein V, that reacts with all four subclasses of human IgG. Specifically, protein V reacts with the Fc portion of human immunoglobulin G (IgG). The protein also binds, non-specifically, IgG from other mammalian species including rabbit, swine, horse, bovine, sheep, and goat. Protein V does not bind mouse, chicken or human IgM immunoglobulin. The activity of protein V is inhibited with proteinase K.

A second aspect of the present invention is a method of producing Protein V, and the Protein V so produced, which comprises: (a) extracting a crude protein preparation from *Gardnerella vaginalis* cells; and then (b) purifying the proteinaceous factor which binds human $IgG_1$, human $IgG_2$, human $IgG_e$, and human $IgG_4$ from the crude protein preparation.

A third aspect of the present invention is a recombinant DNA sequence comprising vector DNA and a DNA encoding the Protein V.

A fourth aspect of the present invention is a host cell containing a recombinant DNA sequence described above and capable of expressing the Protein V.

A fifth aspect of the invention is an improved method of making the Protein V, which comprises culturing the host cell expressing Protein V and harvesting said Protein V from the culture.

The foregoing and other aspects of this invention are explained in the Figures, Detailed Description, and Experimental sections set forth below.

DETAILED DESCRIPTION OF THE INVENTION

Figure 1:
FIG. 1. *Dot Blot Analysis.* Non-specific binding of Ig to strain #AB107 Whole cells —Goat IgG-HRP; 2. —Swine IgG-HRP; 3. —Human IgM (whole antibody) HRP; 4. —Human IgG (Fc)-HRP; 5. —Human IgG-F(a,b')$_2$.

Protein V is isolated from *Gardnerella vaginalis*. The term "*G. vaginalis*", as used herein, is intended to encompass both *Haemoohilus vaginalis* and *Corynebacterium vaginale*, in accordance with currently accepted usage. See D. Yong and J. Thompson, *J. Clin. Microbiol.* 16: 30–33 (1982); see also P. Piot et al., *J. Gen. Microbiol.* 119: 373–396 (1980).

Protein V is also obtained from certain unclassified coryneform organisms morphologically resembling *G. vaoinalis*. The unclassified coryneform organisms (UCOs) that are the source Protein V are catalase-negative bacteria morphologically resembling *G. vaqinalis*, but are not beta-hemolytic on human blood agar. See P.

Piot et al., *J. Clin Microbiol.* 15: 19-24 (1982). They may be specifically identified as Unclassified Coryneform Organisms of Taxon Cluster 9 in the classification of P. Piot et al., *J. Gen. Microbiol.* 119; 373-396 (1980). In the classification of P. Piot et al., *G. Vaginalis* is identified as belonging to Taxon Cluster 8. The classification of these organisms is not entirely settled. See D. Yong and J. Thompson, *supra; see also Bailey & Scott's Diagnostic Microbiology.* 575-587 (E. Baron and S. Finegold Eds., 8th Ed. 1990)(C.V. Mosby Co., St. Louis, MO). For present purposes, both *G. vaginalis* of Piot's taxon cluster 8 and UCO's of Piot's taxon cluster 9 will be referred to herein simply as "*G. vaginalis*" unless, from the context in which the terms are used, it is apparent that these two groups are being defined separately. Particularly preferred for carrying out the present invention is the strain of Piot's taxon cluster 9 designated as strain no. AB107 herein, and strains having the identifying characteristics of Strain no. AB107. Strain no. AB107 has been deposited with the American Type Culture collection as discussed below.

The present invention also provides methods for isolating and purifying protein V from suitable bacteria. Protein V can be solubilized from suitable bacteria, or crude fragments of suitable bacteria, with common reagents including SDS, mutanolysin and cyanogen bromide/HCl. Thus, a variety of extraction procedures are applicable for isolating protein V, including treatment of whole cells with sodium dodecyl sulfate, aqueous HCl/cyanogen bromide, and mutanolysin. A suitable cyanogen bromide extraction is shown in U.S. Pat. No. 4,945,157 to Boyle and Faulmann and other suitable extraction procedures are given in U.S. Pat. No. 4,883,754 (applicants specifically intend that the disclosure of this and all other patent references cited herein be incorporated herein by reference).

Mutanolysin and aqueous HCl/cyanogen bromide extracts of Protein V are further purified with anion-exchange, high performance, liquid chromatography. The appropriate peak can be identified by its ability to bind IgG, or as described in the Experimental section below. The peak containing Protein V, when concentrated and applied to an electrophoretic gel and Western blot, shows affinity for non-specific antibody. Crude extracts of protein V are visualized on SDS-PAGE gels and transfer to nitrocellulose membranes.

Thus, a method of the present invention for isolating protein V comprises (a) lysing suitable bacterial cells; (b) extracting the lysate with a suitable reagent (e.g., one selected from the group of mutanolysin and aqueous HCl/cyanogen bromide); (c) purifying the crude extract by anion-exchange, high performance liquid chromatography or alternatively extracting the lysate with sodium dodecyl sulfate; (d) further purifying the extract by electrophoresis; and (e) isolating the proteinaceous factor resolving at about 60,000 to about 96,000 daltons.

Protein V of the present invention can also be purified by affinity chromatography on an appropriate immobilized IgG, as described in U.S. Pat. No. 4,883,754.

The present invention also provides methods for purifying or detecting human, and other mammalian, immunoglobulin G. The method comprises mixing the sample from which the immunoglobulin G is to be isolated and purified with a sample containing protein V and isolating the material bound by the proteinaceous factors of the present invention. Known methods for accomplishing such isolation and purification include immobilizing the proteinaceous factors of the present invention on a solid support, contacting the solid support to a crude preparation containing the immunoglobulin to be purified, and then removing the crude preparation from the solid support. Typically, this method is practiced by immobilizing the Protein V on an affinity support in an affinity column, passing a sample containing IgG through the column, and then adding reagents to chemically release the IgG from the immobilized Protein V. Reference can be made to U.S. Pat. No. 3,966,898 to Sjoguist and Sjodin and U.S. Pat. No. 3,995,018 to Sjoguist for various methods of binding IgG with an IgG binding protein. Various embodiments of the foregoing methods can be routinely practiced by those skilled in the art.

Additionally, the proteinaceous factors of the present invention are labeled in order to identify IgG in samples. Accordingly, the proteinaceous factors are labeled with a radioisotope, enzyme, or electron dense ligand. Commonly used radioisotopes suitable for the present purposes include $^{125}I$, $^{131}I$, $^{3}H$, $^{14}C$, and $^{35}S$. Suitable, commonly used enzymes include lactoperoxidase, horseradish peroxidase, alkaline phosphatase, and glucose oxidase. Suitable, commonly used electron dense ligands include ferritin, gold, and horseradish peroxidase. Labelling may be carried out in accordance with procedures known in the art. See, e.g., U.S. Pat. No. 4,883,754.

Suitable bacteria within the scope of this invention include those of natural origin and recombinant origin. The production of cloned genes, recombinant DNA, vectors, transformed host cells, proteins, and protein fragments by genetic engineering is well known. See, e.g., U.S. Pat. No. 4,912,038 to Schilling at Col. 3 line 26 to Col 14 line 12. As an example, in the present invention a DNA sequence comprising a cloned gene or fragment thereof which codes for the production of Protein V is produced by generating Protein V DNA sequences as either a genomic DNA or complementary DNA library. See qenerally S. Primrose, *Principles of Gene Manipulation*, 102-109 (3rd ed. 1985) and T Maniatis et al., *Molecular Cloning: A Laboratory Manual*, 187-246, 270-307 (1982). Small quantities of DNA obtained from library construction and screening are able to be amplified by PCR technology to produce sufficient quantities for cloning into appropriate vectors. See generally U.S. Pat. No. 4,683,195 to Mullis et al. and U.S Pat. 4,683,195 to Mullis.

The production of suitable bacteria requires construction of expression vectors containing the gene for Protein V operably linked to suitable control sequences capable of effecting the expression of Protein V in suitable host cells. The vectors comprise plasmids, viruses, phage, and integratable DNA fragments (i.e. fragments integratable into the host genome by recombination). Whether the vector replicates and functions independently of the host genome or integrates into the host genome itself, expression of the protein is dependent on regions within the vector that are operably linked or functionally associated with the gene coding for the protein V, and are operable in the host organism. Such functional regions ordinarily include an origin of replication (if necessary), a promoter located upstream from the DNA encoding the Protein V, an RNA splice site (if intron-containing genomic DNA is used), a polyadenylation site, and a transcriptional termination sequence. If the vector does not contain a viral origin of replication, the mammalian cells may be transformed with a selectable marker, such as dihydrofolate reductase, and the Protein V DNA. This method is further described in U.S. Pat. No. 4,399,216. A broad variety of suitable prokaryotic and eukaryotic vectors are available. For example, an *Escherichia coli* host is typically transformed using the plasmid pBR322 or its derivative, insect cells are typically transformed with a baculoyirus expression vector such as those derived from *Autograghica californica* MNPV, and mammalian cells are generally transformed with vectors containing a MMTV LTR sequence or SV-40 promoter. Such mammalian vectors are generally inaudible with drugs, such a dexamethasone, as well as capable of conferring selectivity to the host cell by containing a gene encoding resistance to other drugs, such as neomycin.

Transformed host cells, which produce the Protein V upon transformation or transfection with the vectors constructed with the gene for Protein V, may be derived from mammalian or insect sources. Propagation of such cells in cell culture has become a routine procedure (Tissue Culture, Academic press, Kruse and Patterson, editors (1973)). Examples of suitable mammalian cells include VERO, HeLa, CHO, Wl138, BHK, COS-7, CV, and MDCK cell lines, while insect cells are typically cultured *Spodootera fruoigerda* described in U.S. Pat. Nos. 4,745,051 and 4,879,236 to Smith et al.

Prokaryotic cells are also excellent hosts, and include gram positive and gram negative organisms. A representative group of suitable hosts include *E. coli* W3110 (ATCC 27,325), *E. coli* B, *E. coli* X1776 (ATCC 31,537) and *E. coli* 294 (ATCC 31,446).

Eukaryotic yeast cultures may also be transformed with Protein V encoding vectors. *See eg.* U.S. Pat. No. 4,745,057. *Saccharomyces Cerevisiae* is the most commonly used among lower eukaryotic host microorganisms, although a number of other strains are commonly available. Suitable vectors and promoters for the use in yeast expression are further described in R. Hitzeman et al., EPO Publn. No. 73,657.

Transformants may be screened for the production of Protein V by any convenient procedure. For example, a method may be to first transfer colonies from an agar plate to nitrocellulose filters, and then use an antibody to Protein V in a colormetric assay to determine which colonies are producing the Protein V. Other methods include hybridization selection and in situ hybridization. See generally T. Maniatis et al., supra at 310-352.

As noted above, the present invention provides a method for the production of Protein V from a variety of cell and vector combinations, such as by transforming the host cell with an expression vector containing the gene encoding Protein V. In general, purification of Protein V from these sources comprises culturing a host cell which expresses the protein V and harvesting said protein from the culture. This culture can be carried out in any suitable fermentation vessel, with a growth media and under conditions appropriate for the expression of the Protein V in the chosen host cell. The Protein V is collected directly from the culture media, or the host cells are lysed and the Protein V collected therefrom. The Protein V is then further purified in accordance with known techniques.

Cloned genes of the present invention may code for Protein V of any species of origin, including bacterial, murine, porcine, bovine, feline, and human, but preferably code for Protein V of bacterial origin. DNA sequences which code for Protein V, or any proteinaceous factor having the characteristics of Protein V, but differ in code sequence from the isolated sequences due to degeneracy in the genetic code, are also an aspect of this invention. The genetic degeneracy is well known in the literature. See eg. U.S. Pat. No. 4,757,006 to Toole et al. at Col. 2, Table 1. Therefore, DNA sequences which hybridize to DNA which encodes Protein V from *G. vaoinalis*, whether from different species or due to a degeneracy in the genetic code, are aspects of this invention.

In the following Experimental section there are set forth examples that illustrate procedures, including the best mode, for practicing the present invention. In these examples, "nm" means nanometers, "mm" means millimeters, "ng" means nanograms, "mg" means milligrams, "g" means grams, "$\mu$l" means microliters, "ml" means milliliters, "mmol" means millimoles, "Mm" means milliMolar, "M" means Molar, "G" means gravity, "U" means Units, and temperatures are given in degrees Centigrade unless otherwise indicated.

EXPERIMENTAL

I. Methods

A. Bacteria

Strain No. AB107 was isolated from a patient with bacterial vaginosis. This strain formed small, grayish, non-hemolytic colonies on human blood tween (HBT) agar and sheep blood agar. It was also catalase negative and hydrolysed starch and hippurate. Strain No. AB107 cultured either on HBT Agar plates or in Columbia broth supplemented with 5% fetal calf serum under microaerophilic conditions at 37° C. for 48 hrs. Whole cells of Strain No. AB107 were harvested from broth cultures by centrifugation and washed once with phosphate buffered saline, Ph 7.2 (PBS), and stored at $-20°$ C. until used. Strain No. AB107 was identified according to established morphological and biochemical criteria as belonging the group of unclassified coryneform organisms identified as taxon-cluster 9. See P. Piot et al., *J. Clin. Microbiol.* 15: 10-24 (1982); p, Piot et al., *J. Gen. Microbiol.* 119: 373-396 (1980). Strain No. AB107 has been deposited with the American Type Culture Collection, 12301 Parklawn Dr., Rockville, MD 20852, USA, in accordance with the provisions of the Budapest Treaty on June 13, 1991, and designated as ATCC Deposit No. 55195.

B. Extractions

1. Mutanolysin Extract ion, Aliquots containing approximately 0.25 g of bacteria (wet weight) were extracted with Mutanolysin (Sigma Chemical Co., St. Louis, MO) by the method of Siegel et al., Infect. Immun. 31: 808-815 (1981), with slight modifications. Specifically, enzyme extraction of the bacterial pellet was done in 6.0 ml of buffer containing 2000 U of mutanolysin in 0.05 M $KH_2PO_4$, pH 6.5. Extractions were performed for 4 hours at 37° C. The suspension was then centrifuged at $10,000 \times G$ for 15 minutes. The supernatant was then dialyzed overnight against PBS at 4° C. The crude extract was then concentrated in a collodion bag (75,000 HM cut-off) (Schleicher and Schuell, Inc., Keene, NH) to a volume of approximately 100 $\mu$l and stored at $-20°$ C. until used.

2. Cyanogen Bromide/HCl Extractions. Whole cell pellets (approximately 1.0 g wet Weight) were suspended in 0.1 M HCl with and without reagent grade cyanogen bromide (Pierce Chemical Co., Rockford, Il) at a concentration of 15 mg/ml. After slow stirring for 18 hours at room temperature, the suspensions were spun at 10,000×G for 15 minutes. The supernatant was dialyzed against deionized H$_2$O. The crude extracts were then concentrated in collodion bags to volumes of approximately 100 µl and stored at −20° C until used.

3. High-performance liquid chromatography of CNBr/HCl or mutanolysin crude extracts of Protein V. The chromatographic system used for anion exchange purification of CNBr, HCl or mutanolysin extracts of Protein V consisted of model 510 solvent delivery systems, a model 810 B WISP autosampler, a model 490 UV detector set at 280 nm and a model 840 data and chromatography control station (Waters Chromatography Division, Milford, MA). A Protein-Pak DEAE-5PW anion exchange column (Waters) was equilibrated with 25 mM TrisHCl, pH 7.5 in pump A before injection of up to 80 µl of sample. Pump B contained 25 mM tris-HCl, pH 7.5 with 1.0 M NaCl. Gradient conditions were set at a 30 minutes linear gradient, 0–100% B at a flow rate of 1.0 ml/minute. Fractions of the various peaks were collected and concentrated in collodion bags and stored at −20° C. until use. Identification of the fraction containing purified protein V was accomplished by testing each fraction by dot-blot as described below.

4. Sodium Dodecyl sulfate Extractions. A bacterial pellet of approximately 0.25 g wet weight was boiled in 1.0 ml of 2% SDS in deionized water for 10 minutes. The suspension was centrifuged and the proteins in the supernatant were precipitated by the addition of 0.5 ml of 30% trichloroacetic acid. The pellet obtained by centrifugation was washed once with ethanol and once with acetone. The remaining pellet was stored at −20° C. until use.

C. Immunoylobulins

Human polyclonal IgG subclasses were obtained from the WHO/IUIS Immunoglobulin subcommittee. Polyclonal goat, chicken, rabbit, swine, rabbit and mouse which were conjugated to horse radish peroxidase (HRP) were obtained from Kirkegaard and Perry Laboratories, Inc., Gaithersburg, MD and from Accurate Chemical Co., Westbury, NY.

D. Electroohoresis

All electrophoresis techniques, such as polyacrylamide gel electrophoresis in the presence of sodium dodecyl sulfate (SDS-PAGE) or isoelectric focusing (IEF), were performed with the Phastsystem separation and development unit (Pharmacia, Uppsala, Sweden). See D. Anton and R. Kutny, *J. Biol. Chem.* 262: 2817–2822 (1987); and I. Olsson et al., *Electrophoresis* 9: 16–22 (1988). SDS-PAGE gels, IEF gels, buffer strips, molecular weight and pI standards, Coomassie Blue and silver staining kits were also obtained from Pharmacia. The dimensions of the SDS-PAGE gels were 50×43×0.45 mm. The acrylamide concentration was 4% for the stocking gel and 12.5% for the separation gel. The buffer system in the gels was 0.112 M Tris, 0.112 M acetate, pH 6.4. Buffer strips contained 2% agarose, 0.2 M Tris, 0.2 M N-tris (hydroxymethyl) methyl-glycine, pH 8.1 and 0.55% SDS. The size of the IEF gels were 50×43×0.35 mm. The concentration of acrylamide in IEF the media was 5. The IEF gels contained ampholytes (Pharmalyte, Parmacia) in a pH range of 3–9 or 4–6.5 with a buffereing capacity of 0.02 mmol/ml of gel. Samples for SDS-Page were adjusted to concentrations of approximately 100 ng of protein in sample buffere (10 mM Tris-HCl, 1.0 mM EDTA, 2.5% SDS, 5% 2-mercaptoethanol and boiled for 5 minutes). Samples for IEF were adjusted to concentrations of 10–50 ng in deionized H$_2$O. Sample were applied to gels in a volume of 1.0 µl. All conditions of separation and staining were controlled by the computerized system as outlined in the manual. The duration of each step was controlled by volt x hours (Vh). The maximum voltage, current and power for IEF gels was 2000 V, 25 mA, and 7 W and for SDS-PAGE gels was 250 V, 10 mA and 3 W. All gels were run at a constant temperature of 15° C. Staining procedures such as Coomassie Brilliant Blue and silver staining were automatically performed in the development unit according to manufacturers instructions and have been descried elsewhere. D Anton and R. Kutny, supra; I. Olsson et al., supra.

E. Western blotting

PhastGel media, being ultra-thin (SDS-PAGE-0.45 mm, IEF-0.35 mm) were particularly suitable for diffusion blotting according to the method of Beisiegel. See I. Olsson et al., supra. Diffusion blotting was performed by placing a Imobilon-NC nitrocellulose membrane (Cat # HAHY 13250, Millipore Corp., Bedford, MA), which had been cut to the exact dimensions of the separation gel, on the gel surface. For SDS-PAGE gels the transfer was incubated at 70° C. for 20 minutes. IEF gel transfers were incubated at room temperature for 20 minutes. After transfer, the membranes were place in Milk Diluent/Blocking Solution (Kirkegaard & Perry Laboratories, Inc., Gaithersburg, MD) for 1.0 hour. The membranes were then washed in 0.02% Tween-20 for 30 minutes. The membranes were probed with Anitbody-Horse Rasish peroxidase conjugates for 1.0 hour at a dilution of 1:1000 in washing buffer. When the unconjugated, human Ig subclasses were used as first antibody, a second probing followed with chicken anti-human antibody conjugated to HRP. After probing, the membranes were washed three times for 15 minutes each. The membranes were then developed with a solution of 3,3′,5,5′-Tetramethylbenzidine (TMB membrane peroxidase substrate kit, Kirkegaard & Perry Laboratories, Inc.).

F. Dot Blotting

Whole cells of strain #AB107 were washed once in PBS and adjusted to a concentration of 1×10$^8$ cells/ml. the concentration of organisms was standardized by measuring the Optical /Density at 550 nanometers (OD550). Dot blots were performed by using the Bio-Rad bio-dot microfiltration apparatus (Bio-Rad laboratories, Richmond, CA). Nitrocelulose membranes (0.45um, Bio-Rad) were soaked 20 mM Tris, 500 mM NaCl pH 7.5 (TBS) and placed in the apparatus. Whole cell suspensions (100 µl) were pipetted into the wells. Serial dilutions of bacteria were applied to establish optimal binding conditions. After washing the bactyeris in each well with TBS containing 0.5% Tween 20 (U.S. Biochemical Corp., Cleveland, OH), the nitrocellulose was removed and washed thee times, for 15 minutes each time, in 100 ml of TBS-tween 20. The nitrocelulose membrane was then probed and developed as described in the Western blotting procedure.

G. Protein Concentrations

Total protein concentrations were measured with the BCA protein concentration assay (Pierce Chemical Co., Rockford, IL, USA).

II. RESULTS

Whole cell suspensions of strain #AB107, when bound to nitrocellulose membranes and probed with horse radish peroxidase conjugates of various non-specific immunoglobulins in the manner described above, demonstrate strong affinity for Human IgG-Fc fragments, goat IgG and swine IgG whole antibody as shown in figure 1. No affinity was observed for Human IgM whole antibody. Protein V demonstrates weak affinity for Human IgG-F(ab')$_2$ fragments.

Figure 2:
FIG. 2. *SDS-PAGE and Western Blot of Protein V Extracts.* Lane A—E, SDS-PAGE of a 10-15% gradient gel and Lane F—I, Western Blot probed with goat IgG-HRP. Lane A—SDS extract; lane B—aqueous HCl extract; lane C—Cyanogen Bromide extract; lane D—Mutanolysin extract; lane E—Molecular weight standards (molecular weights in kilodaltons); lane F—Mutanolysin extract; lane G—Cyanogen Bromide; lane H—aqueous HCl; lane I—SDS-extract.
Figure 2:
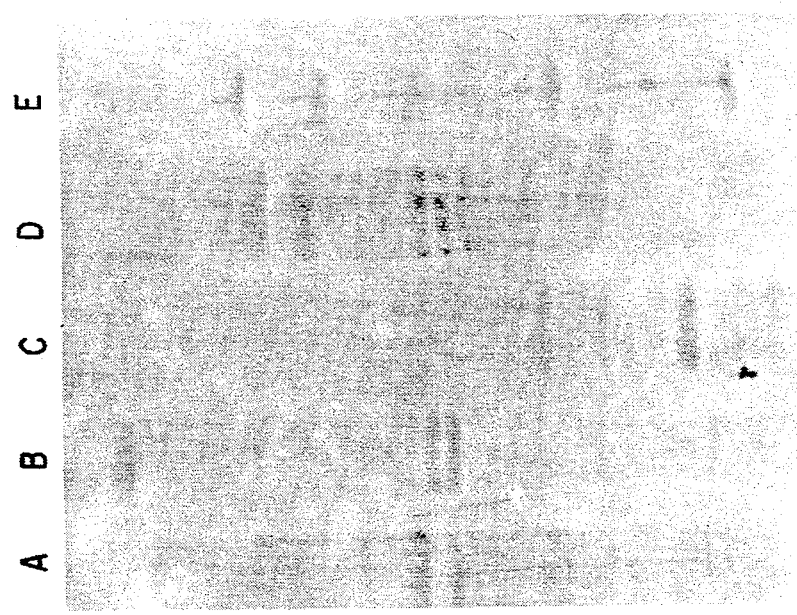
Figure 3:
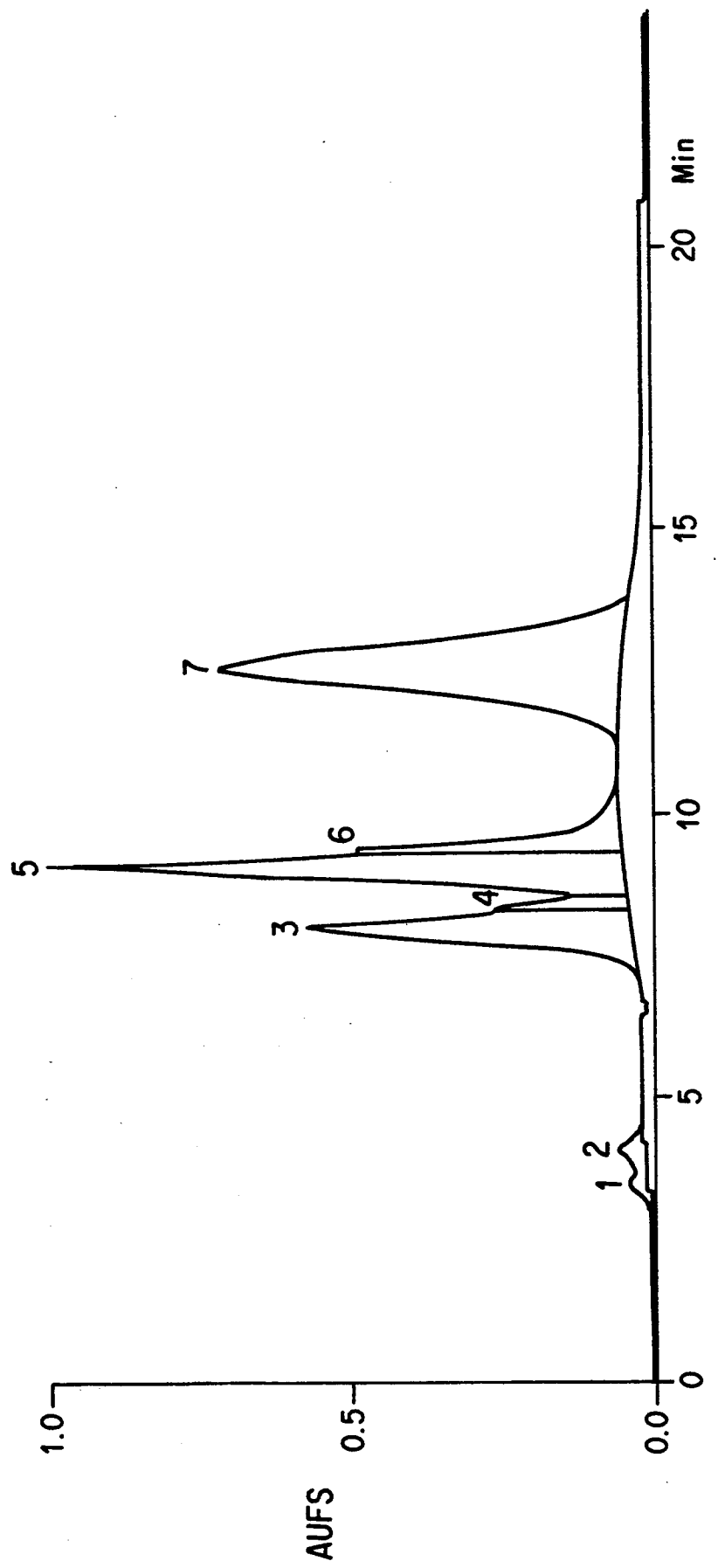
FIG. 3. *Anion Exchange, High Performance Liquid Chromatography of Aqueous HCl Extract of Protein V.* AUFS—absorbance units full scale, detector at 280nm mins—elution in minutes.

Protein V could be solubilized with many extraction methods including SDS, Mutanolysin and cyanogen bromide, as described above. Crude extracts of Protein V could be visualized on SDS-PAGE gels, (figure 2, lanes A-E) and could be transferred to nitrocellulose membranes, as also described above. In FIG. 2, lanes F-I, IgG binding bands on Western blots ranged in size from 96,000 daltons to 60,000 daltons as compared to commercial molecular weight standards (data not shown). Mutanolysin, HCl and cyanogen bromide extracts were further purified with anion-exchange, high performance, liquid chromatography. A typical chromatograph, as shown in FIG. 3, yielded several peaks. Peak number 7, when concentrated and applied to an electrophoretic gel and Western blot, showed affinity for non-specific antibody.

Western blots of crude or purified extracts of protein V always revealed a strong band at 96,000 daltons. There were also successive bands at lower molecular weights. These could be degradation products, resulting from the extraction procedures, which retain the entire immunoglobulin binding receptor. CNBr extracts (FIG. 2, lane G) were more resolved at 96,000 daltons but revealed distinct bands in Western blots ranging from 96,000 daltons to 60,000 daltons.

The binding characteristics of Protein V are summarized in Table 1.

TABLE 1

| | Interactions Between Protein V and Immunoglobulins from Different Species | |
|---|---|---|
| Species | Ig class or Subclass | Binding to Protein V* |
| Human | IgM | − |
| | IgG F(ab')2 | + |
| | IgG Fc | +++ |
| | IgA | − |
| | IgG$_1$ (Kappa) | +++ |
| | IgG$_1$ (Lambda) | +++ |
| | IgG$_2$ (Kappa) | +++ |
| | IgG$_2$ (Lambda) | +++ |
| | IgG$_3$ (Kappa) | +++ |
| | IgG$_3$ (Lambda) | +++ |
| | IgG$_4$ (Kappa) | +++ |
| | IgG$_4$ (Kappa) | +++ |
| Rabbit | IgG | +++ |
| Goat | IgG | +++ |
| Horse | IgG | +++ |
| Sheep | IgG | +++ |
| Swine | IgG | +++ |
| Bovine | IgG$_1$ | − |
| | IgG$_2$ | +++ |
| Mouse | IgG | − |
| Chicken | IgG | − |

*(+++) = strong reaction
(+) = weak reaction,
(−) = no reaction

The functionally active Fc receptor was physicochemically heterogeneous, being resolved into one major band (96,000 daltons) on non-denaturing gels for all extracts except CNBr extracts and into one major band (96,000 daltons) and up to three diffuse bands (90,000 to 60,000 daltons) on SDS polyacrylamide gels.

Despite the obvious heterogeneity in the size of the solubilized Fc receptor, it demonstrated remarkable uniformity in binding to the Fc region of IgG.

The foregoing is illustrative of the present invention, and not to be construed as limiting thereof. The invention is defined by the following claims, with equivalents of the claims to be included therein.

What is claimed is:

1. A purified proteinaceous factor obtained from *Gardnerella vaginalis*, which factor is a receptor for the Fc region of human IgG, which factor binds human IgG$_1$, human IgG$_2$, human IgG$_3$, and human IgG$_4$, and which factor resolves into one major band on non denaturing gels at about 96,000 daltons.

2. The proteinaceous factor of claim 1 immobilized on an inert solid support.

3. The proteinaceous factor of claim 1 labeled with a detectable group selected from the group consisting of radioisotopes, enzymes, and electron dense ligands.

4. The proteinaceous factor of claim 1 labeled with a radioisotope selected from the group consisting of $^{125}$I, $^{131}$I, $^3$H, $^{14}$C, and $^{35}$S.

5. The proteinaceous factor of claim 1 labeled with an enzyme selected from the group consisting of lactoperoxidase, horseradish peroxidase, alkaline phosphatase, and glucose oxidase.

6. The proteinaceous factor of claim 1 labeled with an electron dense ligand selected from the group consisting of ferritin, gold, and horseradish peroxidase.

7. A purified proteinaceous factor having the following identifying characteristics:
 (a) is isolated from *Gardenerella vaginalis;*
 (b) reacts with the Fc protion of human immunoglobulin g;
 (c) possesses affinity for all four subclasses of human IgG;
 (d) possesses non-specific affinity for a broad range of mammalian IgG, including rabbit, swine, horse, bovine, sheep and goat;
 (e) has a molecular weight of about 96,000 on non-denaturing gels; and
 (f) demonstrates inhibited activity in the presence of Proteinase K.

* * * * *

UNITED STATES PATENT AND TRADEMARK OFFICE
CERTIFICATE OF CORRECTION

PATENT NO. : 5,128,451

DATED : 7 July 1992

INVENTOR(S) : John W. Allen

It is certified that error appears in the above-identified patent and that said Letters Patent is hereby corrected as shown below:

Title, please change "PROTEIN V: A IGG BINDING FACTOR" to read --PROTEIN V: A NOVEL IGG BINDING FACTOR".

Column 1, line 39, please change "32" to --132--.

Column 2, line 18, please change "$G_e$" to --$G_3$--.

Column 2, line 36, FIG. 1, please add after Whole cells --1.--.

Column 2, line 58, please change "Haemoohilus" to --Haemophilus--.

Column 2, line 65, please change "vaoinalis" to --vaginalis--.

Column 4, line 40, please change "qenerally" to --generally--.

Column 5, line 7, please change "baculoyirus" to --baculovirus--.

Column 5, line 12, please change "inaudible" to --inducible--.

Column 5, line 25, please change "fruoigerda" to --frugiperda--.

Column 6, line 7, please change "vaoinalis" to --vaginalis--.

Column 6, line 40, please change "p, Piot" to --P, Piot--.

UNITED STATES PATENT AND TRADEMARK OFFICE
CERTIFICATE OF CORRECTION

PATENT NO. : 5,128,451
DATED : 7 July 1992
INVENTOR(S) : John W. Allen

It is certified that error appears in the above-identified patent and that said Letters Patent is hereby corrected as shown below:

Column 6, line 49, please change "Extract ion" to --Extraction--.

Column 7, line 26, please change "sulfate" to --Sulfate--.

Column 7, line 45, please change "D. Electroohoresis" to --D. Electrophoresis--.

Column 7, line 64, please change "5." to --5%--.

Column 7, line 66, please change "buffereing" to --buffering--.

Column 8, line 23, please change "Imobilon" to --Immobilon--.

Column 8, line 53, please change "Nitrocelulose" to --Nitrocellulose--.

Column 8, line 57, please change "bactyeris" to --bacteria--.

Column 8, line 61, please change "nitrocelulose" to --nitrocellulose--.

Column 10, line 51, please change "Gardenerella" to --Gardnerella--.

Column 10, line 52, please change "protion" to --portion--.

UNITED STATES PATENT AND TRADEMARK OFFICE
CERTIFICATE OF CORRECTION

PATENT NO. : 5,128,451
DATED : 7 July 1992
INVENTOR(S) : John W. Allen

It is certified that error appears in the above-indentified patent and that said Letters Patent is hereby corrected as shown below:

Column 10, line 52, please change "protion" to --portion--.

Signed and Sealed this

Thirty-first Day of August, 1993

Attest:

BRUCE LEHMAN

Attesting Officer     Commissioner of Patents and Trademarks